United States Patent
Godwin

(10) Patent No.: US 10,590,471 B2
(45) Date of Patent: Mar. 17, 2020

(54) TARGET ENRICHMENT BY SINGLE PROBE PRIMER EXTENSION

(71) Applicant: ROCHE SEQUENCING SOLUTIONS, INC., Pleasanton, CA (US)

(72) Inventor: Brian Christopher Godwin, Livermore, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 358 days.

(21) Appl. No.: 15/228,806

(22) Filed: Aug. 4, 2016

(65) Prior Publication Data

US 2017/0037459 A1 Feb. 9, 2017

Related U.S. Application Data

(60) Provisional application No. 62/201,727, filed on Aug. 6, 2015.

(51) Int. Cl.
 C12Q 1/6853 (2018.01)
 C12Q 1/6869 (2018.01)
 C12Q 1/6855 (2018.01)

(52) U.S. Cl.
 CPC ......... *C12Q 1/6853* (2013.01); *C12Q 1/6855* (2013.01); *C12Q 1/6869* (2013.01)

(58) Field of Classification Search
 None
 See application file for complete search history.

(56) References Cited

U.S. PATENT DOCUMENTS

| | | | |
|---|---|---|---|
| 8,932,831 B2 | 1/2015 | Korfhage et al. | |
| 9,315,863 B2 | 4/2016 | Nadeau | |
| 9,546,399 B2 | 1/2017 | Amorese et al. | |
| 2005/0123956 A1* | 6/2005 | Blume | C12Q 1/6809 435/6.12 |
| 2005/0191682 A1* | 9/2005 | Barone | C12Q 1/6806 435/6.11 |
| 2007/0020640 A1 | 1/2007 | McCloskey et al. | |
| 2009/0105959 A1* | 4/2009 | Braverman | C12Q 1/68 702/19 |
| 2012/0289414 A1* | 11/2012 | Mitra | C12P 19/34 506/4 |
| 2013/0231253 A1 | 9/2013 | Amorese et al. | |
| 2013/0303461 A1 | 11/2013 | Lafrate et al. | |
| 2014/0193860 A1* | 7/2014 | Bevilacqua | C12Q 1/6806 435/91.52 |
| 2015/0119261 A1 | 4/2015 | Richard | |
| 2015/0211050 A1 | 7/2015 | Lafrate et al. | |
| 2016/0203259 A1 | 7/2016 | Scolnick et al. | |
| 2016/0222427 A1 | 8/2016 | So et al. | |
| 2017/0016056 A1 | 1/2017 | Tan et al. | |

FOREIGN PATENT DOCUMENTS

| | | | |
|---|---|---|---|
| WO | WO-2013138536 A1 * | 9/2013 | ............... C12Q 1/68 |
| WO | 2016118719 A1 | 7/2016 | |

OTHER PUBLICATIONS

Jabara CB, Jones CD, Roach J, Anderson JA, Swanstrom R. Accurate sampling and deep sequencing of the HIV-1 protease gene using a Primer ID. Proc Natl Acad Sci U S A. Dec. 13, 2011; 108(50):20166-71. Epub Nov. 30, 2011. (Year: 2011).*

Meyer et al. A high-coverage genome sequence from an archaic Denisovan individual. Science. Oct. 12, 2012; 338(6104):222-6. Epub Aug. 30, 2012. (Year: 2012).*

Jabara et al. Supplemental Information. (2011, PNAS, 108(50):20166-71; pp. 1-9). (Year: 2011).*

Meyer et al. A (2012, Supplemental Information, Science 338(6104):222-6. pp. 1-146). (Year: 2012).*

Croucher NJ, Fookes MC, Perkins TT, Turner DJ, Marguerat SB, Keane T, Quail MA, He M, Assefa S, Bähler J, Kingsley RA, Parkhill J, Bentley SD, Dougan G, Thomson NR. A simple method for directional transcriptome sequencing using Illumina technology. Nucleic Acids Res. Dec. 2009; 37(22):e148. (Year: 2009).*

Hashimshony T, Wagner F, Sher N, Yanai I. CEL-Seq: single-cell RNA-Seq by multiplexed linear amplification. Cell Rep. Sep. 27, 2012; 2(3):666-73. Epub Aug. 30, 2012. (Year: 2012).*

Gansauge MT, Meyer M. Single-stranded DNA library preparation for the sequencing of ancient or damaged DNA. Nature protocols. Apr. 2013; 8(4):737. (Year: 2013).*

Kwok CK, Ding Y, Sherlock ME, Assmann SM, Bevilacqua PC. A hybridization-based approach for quantitative and low-bias single-stranded DNA ligation. Analytical biochemistry. Apr. 15, 2013; 435(2):181-6. (Year: 2013).*

Bybee SM, Bracken-Grissom H, Haynes BD, Hermansen RA, Byers RL, Clement MJ, Udall JA, Wilcox ER, Crandall KA. Targeted amplicon sequencing (TAS): a scalable next-gen approach to multilocus, multitaxa phylogenetics. Genome Biol Evol.2011; 3:1312-23. Epub Oct. 13, 2011. (Year: 2011).*

Binladen J, Gilbert MT, Bollback JP, Panitz F, Bendixen C, Nielsen R, Willerslev E. The use of coded PCR primers enables high-throughput sequencing of multiple homolog amplification products by 454 parallel sequencing. PloS one. Feb. 14, 2007; 2(2): e197: pp. 1-9. (Year: 2007).*

(Continued)

*Primary Examiner* — Gary Benzion
*Assistant Examiner* — Olayinka A Oyeyemi
(74) *Attorney, Agent, or Firm* — Olga Kay

(57) ABSTRACT

The invention comprises methods and compositions for enriching for a target nucleic acid with a single primer extension and low-bias limited amplification.

10 Claims, 2 Drawing Sheets

(56) References Cited

OTHER PUBLICATIONS

Ding Y, Tang Y, Kwok CK, Zhang Y, Bevilacqua PC, Assmann SM. In vivo genome-wide profiling of RNA secondary structure reveals novel regulatory features. Nature. Jan. 30, 2014; 505(7485):696-700. Epub Nov. 24, 2013. (Year: 2013).*

Ding Y, Kwok CK, Tang Y, Bevilacqua PC, Assmann SM. Genome-wide profiling of in vivo RNA structure at single-nucleotide resolution using structure-seq. Nat Protoc. Jul. 2015; 10(7):1050-66. Epub Jun. 18, 2015. (Year: 2015).*

Parkhomchuk D, Borodina T, Amstislayskiy V, Banaru M, Hallen L, Krobitsch S, Lehrach H, Soldatov A. Transcriptome analysis by strand-specific sequencing of complementary DNA. Nucleic Acids Res. Oct. 2009; 37(18):e123 pp. 1-7. Epub Jul. 20, 2009. (Year: 2009).*

Hou Z, Jiang P, Swanson SA, Elwell AL, Nguyen BK, Bolin JM, Stewart R, Thomson JA. A cost-effective RNA sequencing protocol for large-scale gene expression studies. Sci Rep. Apr. 1, 2015; 5:9570 pp. 1-5. (Year: 2015).*

Hou et al. Supplemental Information. pp. 1-10. Sci Rep. Apr. 1, 2015; 5:9570. (Year: 2015).*

Gupta et al, 2005, "Synthesis and surface engineering of iron oxide nanoparticles for biomedical applications", Biomaterials, 26:3995-4021.

Kim et al, 2008, "Multifunctional Uniform Nanoparticles Composed of a Magnetite Nanocrystal Core and a Mesoporous Silica Shell for Magnetic Resonance and Fluorescence Imaging and for Drug Delivery", Angewandte Chemie International Edition, 48:8438-8441.

Liu et al, 2010, "Shape Evolution and Tunable Properties of Monodisperse Magnetite Crystals Synthesized by a Facile Surfactant-Free Hydrothermal Method", European Journal of Inorganic Chemistry, 4499-4505.

Narayanan et al, Enhanced Bio-Coompatibility of Ferrofluids of Self-Assembled Superparamagnetic Iron Oxide-Silica core-Shell Nanoparticles, Journal of Nanoscience and Nanotechnology, 2011, pp. 1958-1967, vol. 11.

* cited by examiner

FIGURE 2

Removal of non-extended DNA
- 5'-exo if original primer has a 5'-block
- ssDNA endo if primer is protected, dsDNA will remain (not shown)

3. Exonuclease addition

Gene Sp. 1 UID

3' ssDNA ligation
- Swiss Bio 1S kit
- Penn State hairpin

4. Ligase and adaptor addition

Universal Primer A

UID  MID

Ligate

Ligate

LM PCR

5. PCR reagents and thermocycle

Universal Primer B →       ← Universal Primer A

UID  MID

TARGET ENRICHMENT BY SINGLE PROBE PRIMER EXTENSION

FIELD OF THE INVENTION

The disclosure relates generally to enrichment of nucleic acid targets in a sample and more particularly, to enrichment of targets for nucleic acid sequencing, including high throughput sequencing.

BACKGROUND OF THE INVENTION

The invention belongs to a class of technologies that allow users to focus on regions of interest within the nucleic acid to be sequenced. This lowers costs associated with sequencing reactions and subsequent data analysis. There are currently three general types of technologies that selectively capture regions of interest within a nucleic acid present in a sample. The first technology is hybridization capture wherein regions of interest are captured through the hybridization of a probe that can be selectively bound to a capture surface. This capture allows for the removal of non-target nucleic acids followed by a release and collection of the captured target molecules. This type of technology has advantages including the ability to capture exome-sized regions and regions that contain unknown structural variations. The disadvantages include long and complex protocols that tend to take well over 8 hours to complete. The complexity is primarily caused by the requirement to prepare a randomly fragmented shotgun library prior to hybridization. The hybridization step alone can take up to three days to complete. Examples of this type of technology include SeqCap EZ (NimbleGen, Madison, Wis.) and Sure-Select Target Enrichment System (Agilent, Santa Clara, Calif.)

Another method of target enrichment is dual-target primer based amplification. In this method, regions of interest are enriched using two probes on the boundaries of the target. The methods tend to take less than 8 hours to complete and are simpler than hybridization capture methods. However, dual primer based technologies are not capable of enriching sequences with unknown structural variations. The most established dual primer approach is multiplex PCR. It is a very simple single step process but is only capable of amplifying tens of targets per reaction tube. Other newer technologies are currently available, including TruSeq Amplicon (Illumina, San Diego, Calif.) and Ion Torrent Ampliseq (Life Technologies, Grand Island, N.Y.) products which are capable of amplifying hundreds to thousands of targets in a single reaction tube and require only a few handling steps.

The third technology is single-target primer based amplification. In this method, targets are enriched through the amplification of a region that is defined by a single target primer and an end-ligated universal primer. Similar to the hybridization based approach; these technologies require a randomly fragmented shotgun library to be generated prior to the selective hybridization of a target oligonucleotide. However, instead of using this oligonucleotide to capture the target and wash away non-target molecules, an amplification step is employed which selectively amplifies regions between the randomly-generated end and the target specific oligonucleotide. The advantage of this technology is that unlike dual primer technologies, it allows for the detection of sequences with unknown structural variations. It is also faster and simpler than hybridization based technologies. However, this type of technology is still slower and more complicated than dual primer based approaches. Examples of this type of technology are Archer's Anchored Multiplex PCR (Archer Dx, Boulder, Colo.) and Ovation Target Enrichment System (NuGen, San Carlos, Calif.).

There remains an unmet need for a fast and simple method of target enrichment that would also accommodate for unknown structural variations in a target sequence.

SUMMARY OF THE INVENTION

In one embodiment, the invention is a method of amplifying a target sequence comprising the steps of contacting the target nucleic acid with a primer and a polymerase, where the primer comprises a target-binding site and a unique molecular identification tag (UID); conducting a polymerase extension reaction and a termination to create a single-stranded primer extension product; ligating adaptors to each end of the single-stranded primer extension product to create a ligation product, wherein adaptors comprise at least one universal priming site; amplifying the ligation product in an amplification reaction utilizing at least one primer binding to the at least one universal priming site to create the amplified target sequence. In some embodiments, the primer and at least one of the adaptors comprise mutually compatible universal ligation sites. In some embodiments, the target-binding site is a pre-designed target-specific sequence. In some embodiments, the target-binding site is a random sequence. In some embodiments, the termination is effected by a method selected from the list consisting of temperature shift, addition of a specific enzyme inhibitor, addition of a chelator, incorporation of uridine-containing bases followed by treatment with uracil-N-DNA glycosylase. In some embodiments, at least one adaptor comprises a barcode. The barcode can be a multiplex sample ID (MID). The amplification can be linear amplification or exponential amplification. In some embodiments, the method further comprises a purification step after at least one of primer extension and ligation.

In other embodiments, the invention is a kit for amplifying a target sequence comprising: a primer comprising a target-binding site, a unique molecular identification tag (UID), and a universal ligation site; at least one adaptor comprising at least one universal priming site, multiplex sample ID (MID) and a universal ligation site. In some embodiments, the kit comprises two adaptors having different universal priming sites but only one adaptor comprising the universal ligation site and the MID. In some embodiments, the kit further comprises one or more of the following: nucleic acid polymerase, ligase, thermostable DNA polymerase, and universal primers.

BRIEF DESCRIPTION OF THE DRAWINGS

FIG. 2 is a schematic representation of steps 3-5 of the method of the invention.

DETAILED DESCRIPTION OF THE INVENTION

Definitions

Figure 1:
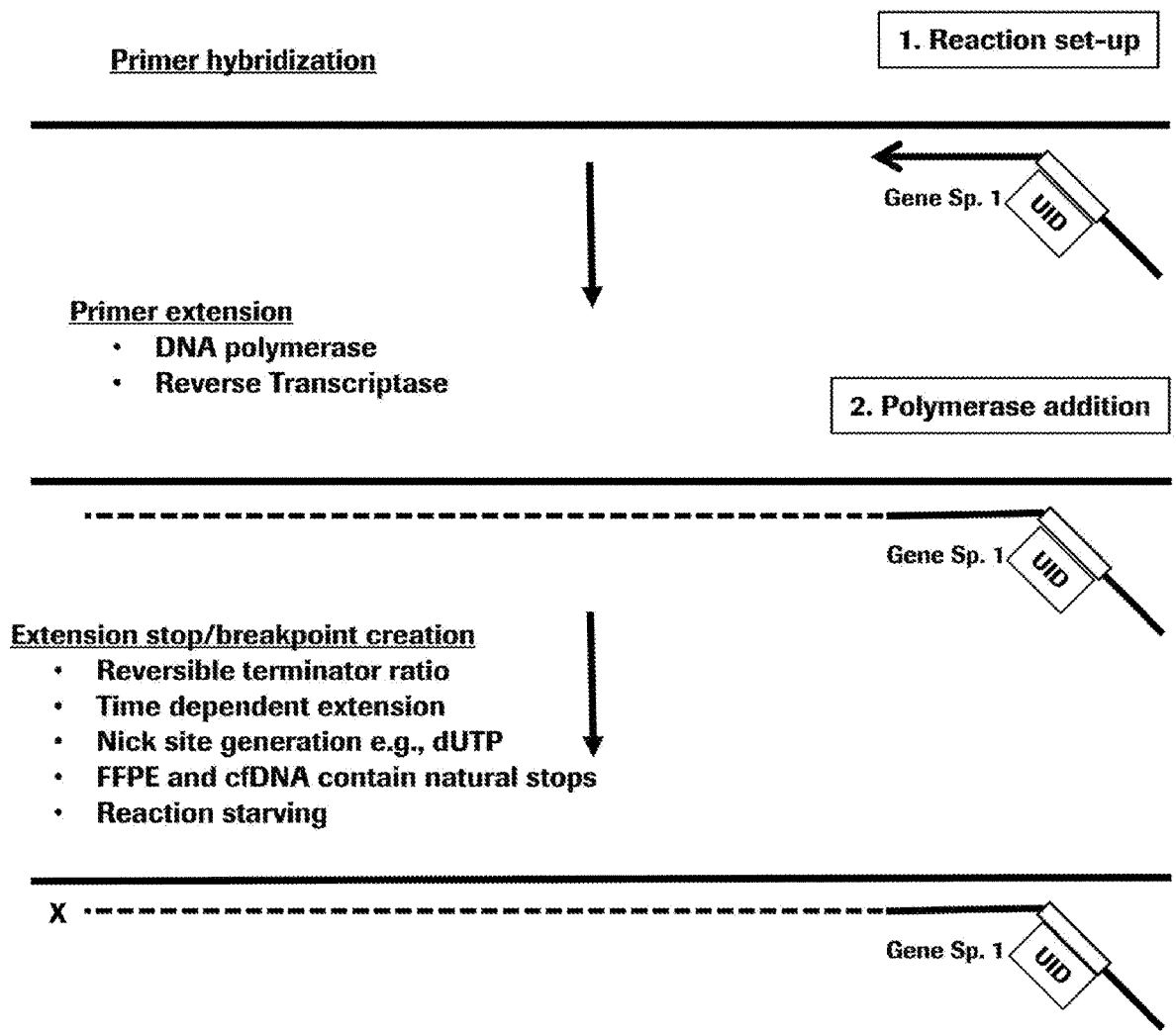
FIG. 1 is a schematic representation of steps 1-2 of the method of the invention.

As used herein, "probe" means any molecule that is capable of selectively binding to a specifically intended target biomolecule, for example, a nucleic acid sequence of interest to be bound, captured or hybridized by the probes.

As used herein, "adaptor" means a nucleotide sequence that may be added to another sequence so as to import additional properties to that sequence. An adaptor can be single- or double-stranded, or may have both a single-stranded portion and a double-stranded portion.

As used herein, "barcode" means a nucleotide sequence conferring identity to a molecule. A barcode may confer a unique identity to an individual molecule (and its copies). Such a barcode is a unique ID (UID). A barcode may confer a identity to an entire population of molecules (and their copies) coming from the same source (e.g., a patient). Such a barcode is a multiplex ID (MID).

As used herein, "ligation site" is a portion of a nucleic acid molecule (other than a blunt end of a double stranded molecule) that can facilitate ligation. "Compatible ligation sites" present on two molecules enable preferential ligation of the two molecules with each other.

As used herein, "single-stranded ligation" is a ligation procedure commencing with at least one single-stranded substrate and typically involving one or more double-stranded or partially-double-stranded adaptors.

As used herein, "universal primer" and "universal priming site" refer to a primer and priming site not naturally present in the target sequence. Typically, the universal priming site is present in adaptors or target-specific primers. The universal primer can bind to and direct primer extension from the universal priming site.

The methods of the instant invention can be used as a part of a sequencing protocol, including a high throughput single molecule sequencing protocol. The method of the invention generates a library of target nucleic acids to be sequenced. The target nucleic acids in the library may incorporate barcodes for molecular identification and sample identification.

The present invention comprises a linear primer extension step for the target specific primer. The linear extension step has several advantages over exponential amplification practiced in the art. Each target nucleic acid is characterized by a unique rate of synthesis that depends on the rate of annealing of the target-specific primer and the rate with which a polymerase can read through a particular target sequence. Differences in the rate of extension and the rate of synthesis create a bias that may result in a slight difference in a single round of synthesis. However, the slight difference becomes exponentially amplified during PCR. The resulting gap is referred to as PCR bias. The bias may obscure any difference in the initial quantities of each sequence in the sample and preclude any quantitative analysis.

The present invention limits extension of target-specific primers (including gene-specific primers and degenerate primers that by chance are specific to a binding site within the genome) to a single step. Any exponential amplification is performed with universal primers not subject to template-dependent bias, or subject to a lesser bias than the target-specific primer.

Referring to FIG. 1, the method comprises primer extension. The method includes a reaction set up step (step 1, primer hybridization) followed by a polymerase addition step (step 2, primer extension). Optionally, the primer hybridization and extension steps are performed simultaneously, i.e., as a single step under the same reaction conditions. In other embodiments, the steps are performed separately as a two-step process with distinct reaction conditions.

The primer hybridization step is mediated by the target-specific region of the primer. In some embodiments, the target-specific region is capable of hybridizing to region of a gene located in an exon, intron, or an untranslated portion of a gene or in an untranscribed portion of the gene, e.g., a promoter or an enhancer. In some embodiments, the gene is a protein-coding gene but in other embodiments, the gene is not a protein-coding gene, such as an RNA-coding gene or a pseudogene. In yet other embodiments, the target-specific region is located in an intergenic region. For RNA targets, the primer may comprise an oligo-dT sequence.

Instead of a pre-designed target-specific region, a primer may contain a degenerate sequence, i.e., a string of randomly incorporated nucleotides. Such a primer may also find a binding site within the genome and act as a target-specific primer for that binding site.

In addition to the target-specific region, the primer may comprise additional sequences. In some embodiments, these sequences are located to the 5'-end of the target-specific region. In other embodiments, it may be possible to include these sequences elsewhere within the primer as long as the target-specific region is capable of hybridizing to the target and driving the primer extension reaction as described below. The additional sequences within the primer may include one or more barcode sequences, such as a unique molecular identification sequence (UID) or a multiplex sample identification sequence (MID). The barcode sequences may be present as a single sequence or as two or more sequences.

In some embodiments, the additional sequences include sequences that facilitate ligation to the 5'-end of the primer. The primer may contain a universal ligation sequence that enables ligation of an adaptor as described in the following section.

In some embodiments, the additional sequences include one or more a binding sites for one or more universal amplification primers.

The primer extension step is performed by a nucleic acid polymerase. Depending on the type of nucleic acid being analyzed, the polymerase may be a DNA-dependent DNA polymerase ("DNA polymerase") or an RNA-dependent DNA polymerase ("reverse transcriptase").

In some embodiments it is desired to control the length of the nucleic acid strand synthesized in the primer extension reaction. (FIG. 1, extension stop). As is explained below, the length of this strand determines the length of the nucleic acid subjected to the subsequent steps of the method and any downstream applications. The extension reaction can be terminated by any method known in the art. The reaction may be physically stopped, e.g., by a shift in temperature or addition of a polymerase inhibitor. In some embodiments, the reaction is stopped by placing the reaction on ice. In other embodiments, the reaction is stopped by elevating the temperature to inactivate a non-thermostable polymerase. In yet other embodiments, the reaction is stopped by the addition of a chelator, such as EDTA able to sequester a critical co-factor for the enzyme, or another chemical or biological substance compound able to reversibly or in inactivate the enzyme.

Another method of controlling the length of primer extension products is starving the extension reaction by limiting a critical component (e.g., dNTPs) to directly limit the extension length or $Mg^{2+}$ to slow the rate of extension and improve the capability to control the extension stop point. One skilled in the art is able to experimentally or theoretically determine the proper amount of the critical component that allows for limited primer extension to yield predominantly the desired-length product.

Another method of controlling the length of primer extension products is the addition of terminator nucleotides, including reversible terminator nucleotides. One skilled in the art is able to experimentally or theoretically determine a proper ratio of terminator and non-terminator nucleotides that allows for limited primer extension to yield predominantly the desired length product. Examples of terminator nucleotides include dideoxy nucleotides, 2'-phosphate nucleotides as described in U.S. Pat. No. 8,163,487, 3'-O-blocked reversible terminators, and 3' unblocked reversible terminators as described e.g., in US20140242579 and Guo., J., et al., *Four-color DNA sequencing with 3'-O-modified nucleotide reversible terminators and chemically cleavable fluorescent dideoxynucleotides*, P.N.A.S. 2008 105 (27) 9145-9150. Yet another method of controlling the length of primer extension products is the addition of limited amounts of uracil (dUTP) to the primer extension reaction. The uracil-containing DNA can then be treated with uracil-N-DNA glycosylase to produce abasic sites. The DNA with abasic sites can be degraded by heat treatment with optional addition of alkali to improve the efficiency of degradation as described in U.S. Pat. No. 8,669,061. One skilled in the art is able to experimentally or theoretically determine a proper ratio of dUTP to dTTP in the extension reaction that allows for limited inclusion of dUTP to yield predominantly the desired length product upon endonuclease treatment.

In some embodiments, the length of the extension product is intrinsically limited by the length of the input nucleic acid. For example, cell-free DNA present in maternal blood plasma is below 200 bp in length with the majority being 166 bp long. Yu, S. C. Y., et al., *Size-based molecular diagnostics using plasma DNA for noninvasive prenatal testing*, PNAS USA 2014; 11(23):8583-8. The median length of cell-free DNA found in the plasma of healthy individuals and cancer patients is about 185-200 bp. Giacona, M. B., et al., *Cell-free DNA in human blood plasma: length measurements in patients with pancreatic cancer and healthy controls*, Pancreas 1998; 17(1):89-97. Poorly preserved or chemically treated samples may contain chemically or physically degraded nucleic acids. For example, formalin-fixed paraffin embedded tissues (FFPET) typically yield nucleic acids that average 150 bp in length.

In some embodiments, the method of the invention includes one or more purification steps after the primer extension by DNA polymerase or reverse transcriptase. The purification will remove unused primer molecules and the template molecule used to create the primer extension product. In some embodiments, the template nucleic acid and all nucleic acid fragments other than the extended primer are removed by exonuclease digestion. In that embodiment, the primer used in the primer extension may have a 5'-end modification making the primer and any extension product resistant to exonuclease digestion. Examples of such modification include phosphorothioate linkage. In other embodiments, RNA template can be removed by enzymatic treatment that will spare DNA, e.g., RNase digestion, including RNaseH digestion. In yet other embodiments, the primers and large-size template DNA are separated from the extension products by a size-exclusion method, for example, gel electrophoresis, chromatography or isotachophoresis.

In some embodiments, purification is by affinity binding. In variations of this embodiment, the affinity is to the specific target sequence (sequence capture). In other embodiments, the primer comprises an affinity tag. Any affinity tag known in the art can be used, e.g., biotin or an antibody or an antigen for which a specific antibody exists. The affinity partner for the affinity tag may be present in solution, e.g., on suspended particles or beads, or bound to solid support. In the course of affinity purification, unbound components of the reaction mixture are washed away. In some embodiments, additional steps are taken to remove unused primer.

In some embodiments, the invention includes a ligation step. For example, it is possible to add a homopolymer tail to the 3' end of a nucleic acid. In this embodiment, the homopolymer may serve as a binding site for the reverse complement homopolymer (similar to poly-A tail with poly-T primer for mRNA). The ligation adds one or more adaptor sequences to the primer extension product generated in the preceding step. The adaptor sequence supplies one or more universal priming sites (for amplification or sequencing) and optionally, one or more barcodes. The exact mode of ligating the adaptor is immaterial as long as the adaptor becomes associated with the primer extension product and enables subsequent steps described below.

In some embodiments described above, the method involves a target-specific primer that includes a universal priming sequence ("priming site") and yields a primer extension product with a single priming site. In such embodiments, only one additional priming sequence ("priming site") needs to be provided to enable exponential amplification. In other embodiments, the target-specific primer does not include a universal priming site. In such embodiments, two priming sites need to be provided to enable exponential amplification. The adaptors with universal priming sites may be added by any single-strand ligation methods available in the art.

One example of a single-strand ligation method can be used in embodiments where the extension primer comprises a universal ligation site. In such embodiments, the adaptor having a double-stranded region and a single stranded overhang complementary to the universal ligation site in the primer may be annealed and ligated as shown on FIG. 1, step 4. Annealing of the single stranded 3'-overhang of the adaptor to the universal ligation site at the 5'-end of the primer creates a double stranded region with a nick in the strand containing the primer extension product. The two strands can be ligated at the nick by a DNA ligase or another enzyme, or a non-enzymatic reagent that can catalyze a reaction between the 5'-phosphate of the primer extension product and the 3'-OH of the adaptor. By connecting the adaptor, the ligation provides a universal priming site at one end of the primer extension product.

Another example of a single-strand ligation method can be used to add the universal priming site to the opposite end of the primer extension product (or, in embodiments where the extension primer does not comprise a universal ligation site, to both sides of the extension product). For this embodiment, one or both ends of the primer extension product to be ligated does not have a universal ligation site. Further, in some embodiments, at least one end of the primer extension product to be ligated has an unknown sequence (e.g., due to a random termination event or an unknown sequence variation.). In such embodiment, a sequence-independent single-strand ligation method is employed. An exemplary method is described in a U.S. Application Pub. No. 20140193860. Essentially, the method uses a population of adaptors where the single-stranded 3'-end overhang instead of having a universal ligation site, has a random sequence, e.g., a random hexamer sequence. In some embodiments of that method, the adaptor also has a hairpin structure. Another example is a method enabled by Accel-NGS™ 1S DNA Library Kit (Swift Biosciences, Ann Arbor, Mich.).

The ligation step of the method utilizes a ligase or another enzyme with a similar activity or a non-enzymatic reagent. The ligase can be a DNA or RNA ligase, e.g., of viral or bacterial origin such as T4 or *E. coli* ligase, or thermostable ligases Agu, Taq, Tfl or Tth. In some embodiments, an alternative enzyme, e.g., topoisomerase can be used. Further, a non-enzymatic reagent can be used to form the phosphor-diester bond between the 5'-phosphate of the primer extension product and the 3'-OH of the adaptor as described and referenced in US20140193860.

In some embodiments of the method, the first ligation of the adaptor is followed by an optional primer extension. The ligated adaptor has a free 3'-end that can be extended to create a double-stranded nucleic acid. The end opposite the adaptor will then become suitable for a blunt-end ligation of another adaptor. Avoiding the need for a single-strand ligation procedure, this double stranded end of the molecule can be ligated to a double stranded adaptor by any ligase or another enzymatic or non-enzymatic means. The double stranded adaptor sequence supplies one or more universal priming sites (for amplification or sequencing) and optionally, one or more barcodes.

In some embodiments, the method of the invention includes one or more purification steps after the ligation step. The purification will remove unused adaptor molecules. The adaptors and large-size ligated products are separated from the extension products by a size-exclusion method, for example, gel electrophoresis, chromatography or isotachophoresis.

In some embodiments, purification is by affinity binding, in variations of this embodiment, the affinity is to the specific target sequence (sequence capture). In other embodiments, the adaptor comprises an affinity tag. Any affinity tag known in the art can be used, e.g., biotin or an antibody or an antigen for which a specific antibody exists. The affinity partner for the affinity tag may be present in solution, e.g., on suspended particles or beads, or bound to solid support. In the course of affinity purification, unbound components of the reaction mixture are washed away. In some embodiments, additional steps are taken to remove unused adaptor.

In some embodiments, the invention comprises an amplification step. This step can involve linear or exponential amplification, e.g., PCR. The primers for amplification may include any sequences that are present within the nucleic acid being amplified and can support synthesis of one or both strands, Amplification may be isothermal or involve thermocycling.

In some embodiments, the amplification is exponential and involves PCR. It is desired to reduce PCR amplification bias. If one or more gene-specific primers are used, to reduced bias, the method involves a limited number of amplification cycles, e.g., about 10 or fewer cycles. In other variations of these embodiments, universal primers are used to synthesize both strands. The universal primer sequences may be a part of the original extension primer of one or both ligated adaptors. One or two universal primers can be used. The extension primer and one or both adaptors described above can be engineered to have the same primer binding site. In that embodiment, a single universal primer can be used to synthesize both strands. In other embodiments, the extension primer (or adaptor) on one side and the adaptor on the other side of the molecule to be amplified contain different universal primer binding sites. A universal primer may be paired with another universal primer (of the same or different sequence). In other embodiments, the universal primer may be paired with a gene-specific primer. Because PCR with universal primers has reduced sequence bias, the number of amplification cycles need not be limited to the same extent as in PCR with gene-specific primers. The number of amplification cycles where universal primers are used can be low but also can be as high as about 20, 30 or more cycles.

The invention includes the use of molecular barcodes. The barcodes typically consist of 4 to 36 nucleotides. In some embodiments, barcodes are designed to have a melting temperature within 10° C. or fewer of one another. Barcodes can be designed to form a minimally cross-hybridizing set, i.e., a combination of sequences that under the desired reaction conditions, form as few as possible stable hybrids with one another. Design, placement and use of barcodes for sequence identification and counting and is known in the art. See e.g., U.S. Pat. Nos. 7,393,665, 8,168,385, 8,481,292, 8,685,678, and 8,722,368.

Barcodes can be used to identify each nucleic acid molecule in the sample and its progeny (i.e., a set of nucleic acid molecules that are produced using the original nucleic acid molecule). Such barcodes are "unique IDs" (UIDs).

Barcodes can also be used to identify a sample from which the nucleic acid molecule being analyzed is derived. Such barcodes are "multiplex sample IDs" ("MIDs"). All molecules derived from the same sample share the same MIDs.

Barcodes comprise a unique sequence of nucleotides characteristic of each barcode. In some embodiments, the sequences of barcodes are pre-designed. In other embodiments, the barcode sequences are random. All or some nucleotides within the barcode can be random. A random sequence and a random nucleotide base within a known sequence are referred to as "degenerate sequence" and "degenerate base" respectively. In some embodiments, a molecule comprises two or more barcodes: one for molecular identification (UID) and one for sample identification (MID). Sometimes, the UID or the MID each comprise several barcodes that when taken together, enable identification of the molecule or the sample.

In some embodiments, the number of UIDs in the reaction can be in excess of the number of molecules to be labeled. In some embodiments, one or more barcodes are used to group or bin sequences. For example, in some embodiments, one or more UIDs are used to group or bin sequences, wherein the sequences in each bin contain the same UID, i.e., are an amplicons derived from a single target molecule. In some embodiments, UIDs are used to align sequences. In other embodiments, the target-specific region is used to align sequences. In some embodiments of the present invention, UIDs are introduced in the initial primer extension event while the sample barcodes (MIDs) are introduced in the ligated adapters.

After the ligation has been performed, i.e., after step 4 or the optional step 5 (FIG. 1), the nucleic acid products can be sequenced. Sequencing can be performed by any method known in the art. Especially advantageous is the high-throughput single molecule sequencing. Examples of such technologies include the 454 Life Sciences GS FLX platform (454 Life Sciences, Branford, Conn.) Illumina HiSeq platform (IIlumina, San Diego, Calif.), Ion Torrent platform (Life Technologies, Grand Island, N.Y.), Pacific BioSciences platform utilizing the SMRT (Pacific Biosciences, Menlo Park, Calif.) and any other presently existing or future single-molecule sequencing technology that does or does not involve sequencing by synthesis. In variations of these embodiments, the sequencing utilizes a universal primers site present in one or both adaptor sequences or in one or both primer sequences. In yet other variations of these embodiments, a gene specific primer is used for sequencing.

It is noted however, that the universal primers are associated with reduced sequencing bias compared to the gene specific primers.

In some embodiments, the sequencing step involves sequence aligning. In some embodiments, aligning is used to determine a consensus sequence from a plurality of sequences, e.g., a plurality having the same unique molecular ID (UID). In some embodiments, aligning is used to identify sequence variations, such as single nucleotide variations (SNV). In some embodiments, a consensus sequence is determined from a plurality of sequences all having an identical UID. In other embodiments, UID is used to eliminate artifacts, i.e., variations existing in the progeny of a single molecule (characterized by a particular UID). Such artifacts resulting from PCR errors or sequencing errors can be eliminated using UIDs.

In some embodiments, the number of each sequence in the sample can be quantified by quantifying relative numbers of sequences with each UID among the population having the same multiplex sample ID (MID). Each UID represents a single molecule in the original sample and counting different UIDs associated with each sequence variant can determine the fraction of each sequence variant in the original sample, where all molecules share the same MID. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

A sample used in the method of the invention comprises any individual (e.g., human, patient) or environmental sample containing nucleic acids. The polynucleotides can be extracted from the sample, or the sample can be directly subjected to the methods of the invention. The starting sample can also be extracted or isolated nucleic acids, DNA or RNA. The sample can constitute any tissue or fluid obtained from an organism. For example, the sample may be a tumor biopsy or a blood or plasma sample. In some embodiments, the sample is a formalin fixed, paraffin-embedded (FFPE) sample. The sample may comprise nucleic acids from one or more sources, e.g., one or more patients. In some embodiments, the tissues can be infected with a pathogen and thus contain host's and pathogen's nucleic acids.

Methods of DNA extraction are well-known in the art. See J. Sambrook et al., "Molecular Cloning; A Laboratory Manual," 1989, 2nd Ed., Cold Spring Harbor Laboratory Press: New York, N.Y.). A variety of kits are commercially available for extracting nucleic acids (DNA or RNA) from biological samples (e.g., BD Biosciences Clontech (Palo Alto, Calif.), Epicentre Technologies (Madison, Wis.); Gentra Systems, Inc. (Minneapolis, Minn.); and Qiagen, Inc. (Valencia, Calif.), Ambion, inc. (Austin, Tex.); BioRad Laboratories (Hercules, Calif.); and more.

In some embodiments, the starting sample used in the method of the invention is a library, e.g., a genomic library or an expression library that comprises a plurality of polynucleotides. In other embodiments, a library is created by the method of the invention. With the starting material being a biological sample, the method creates an amplification library, or a collection of amplicons representing variety or sequences. A library can be stored and used multiple time for further amplification or sequencing of the nucleic acids in the library.

EXAMPLES

Example 1 (Prophetic)

Target Enrichment with Gene-Specific Primer and Linear Amplification

Nucleic acids are isolated from a human blood plasma sample using DNeasy Blood & Tissue Kit (Qiagen, Valencia, Calif.). A gene-specific primer is added. The primer is designed having a gene-specific portion hybridizing to exon 19 of the human EGFR gene. The primer also has a 6-mer unique identification sequence (UID) and a universal ligation sequence. The primer is modified at the 5'-terminus to prevent exonuclease digestion. The primer is allowed to hybridize in Isothermal Amplification Buffer (New England Biolabs, Ipswich, Mass., "NEB") at 60° C. for 20 minutes and Bt Polymerase 2.0 (NEB), a non-thermostable DNA polymerase is added and incubated for 20 seconds at 65° C. The reaction is terminated by heat-killing the polymerase at 95° C. for 3 minutes. The template strands of nucleic acid are digested with a combination of the 5' ssDNA specific exonuclease RecJF (NEB) and the 5' dsDNA specific lambda exonuclease. The non-extended primers are removed using Ampure bead purification (Beckman Coulter, Brea, Calif.).

The single strands resulting from primer extension are purified and added into a ligation reaction. Two kinds of ligation adaptors are added. The 5'-adaptor is designed to contain the universal ligation site, a universal primer site for amplification and a universal primer site for sequencing. The 5'-adaptor also contains a multiplex sample ID (MID). The 3'-adaptor is designed to contain a universal primer site for amplification and a universal primer site for sequencing. Single-stranded ligation is performed using reagents from Accel-NGS™ 1S DNA Library Kit (Swift Biosciences, Ann Arbor, Mich.).

The non-ligated adaptors are separated from the ligation products via Ampure purification as described above.

For linear amplification, the ligation products are contacted with a reaction mixture comprising a single universal primer corresponding to the primer binding site in the 3'-terminal adaptor. Following amplification, a sample of the reaction mixture is transferred into the sequencing reaction comprising a universal sequencing primer.

Example 2 (Prophetic)

Target Enrichment with a Degenerate Primer and Exponential Amplification

Nucleic acids are isolated from a human blood plasma sample using DNeasy Blood & Tissue Kit (Qiagen, Valencia, Calif.). A primer containing a degenerate sequence is added. The primer is designed having a random sequence of six nucleotides, a 6-mer unique identification sequence (UID) and a universal ligation sequence. The primer is modified at the 5'-terminus to present exonuclease digestion. The primer is allowed to hybridize is in Isothermal Amplification Buffer (NEB) at 60° C. for 20 minutes and Bst Polymerase 2.0 (NEB), a non-thermostable DNA polymerase is added and incubated for 20 seconds at 65° C. The reaction is terminated by heat killing the polymerase at 95° C. for 3 minutes. The template strands of nucleic acid are digested with a combination of the 5 ssDNA specific exonuclease RecJF (NEB) and the 5' dsDNA specific lambda exonuclease. The non-extended primers are removed using Ampure bead purification as described in Example 1.

The single strands resulting from primer extension are purified and added into a ligation reaction. Two kids of ligation adaptors are added. The 5'-adaptor is designed to contain the universal ligation site, a universal primer site for amplification and a universal primer site for sequencing. The 5'-adaptor also contains a multiplex sample ID (MID). The 3'-adaptor is designed to contain a universal primer site for amplification and a universal primer site for sequencing. Single-stranded ligation is performed essentially as described in the publication US20140193860.

The non-ligated adaptors are removed using Ampure bead purification as described in Example 1.

For exponential amplification, the ligation products are contacted with a PCR reaction mixture comprising a pair of universal amplification primers. Following amplification, a sample of the reaction mixture is transferred into the sequencing reaction comprising a universal sequencing primer.

While the invention has been described in detail with reference to specific examples, it will be apparent to one skilled in the art that various modifications can be made within the scope of this invention. Thus the scope of the invention should not be limited by the examples described herein, but by the claims presented below.

I claim:

1. A method of amplifying a target sequence comprising the steps of:
    a) contacting the target nucleic acid with a primer and a polymerase, wherein the primer comprises a target-binding site and a unique molecular identification tag (UID);
    b) conducting a polymerase extension step comprising incorporation of uridine-containing bases into the primer comprising the UID and performing a strand cleavage step comprising treatment of the primer extension product with uracil-N-DNA glycosylase and cleavage at the abasic sites of the primer extension product;
    c) ligating adaptors to each end of a single-stranded primer extension product comprising the UID, to create a ligation product, wherein adaptors comprise at least one universal priming site;
    d) amplifying the ligation product in an amplification reaction utilizing at least one primer binding to the at least one universal priming site to create the amplified target sequence.

2. The method of claim 1, wherein the primer extension product in step c) is ligated to an adaptor having a double-stranded region and a single stranded overhang complementary to a ligation site in the primer.

3. The method of claim 1, wherein the target-binding site is a pre-designed target-specific sequence.

4. The method of claim 1, wherein the target-binding site is a random sequence.

5. The method of claim 1, wherein at least one adaptor comprises a barcode.

6. The method of claim 5, wherein the barcode is a multiplex sample identification (MID).

7. The method of claim 1, wherein the amplification in step d) is linear amplification with a universal primer.

8. The method of claim 1, wherein the amplification in step d) is exponential amplification with two universal primers.

9. The method of claim 1, further comprising a purification step after at least one of the steps b) and c).

10. The method of claim 1, wherein the primer extension product in step c) is ligated to an adaptor having a double-stranded region and a single stranded overhang comprising a random sequence.

* * * * *